United States Patent [19]

Akiyama et al.

[11] 4,137,906
[45] Feb. 6, 1979

[54] CATHETER APPARATUS WITH OCCLUSION AND FLOW DIVERTING MEANS

[75] Inventors: Taichiro Akiyama; Haruomi Muto, both of Tokyo, Japan

[73] Assignee: Koken Co., Ltd., Tokyo, Japan

[21] Appl. No.: 794,057

[22] Filed: May 5, 1977

[51] Int. Cl.² .................... A61B 6/00; A61M 25/00
[52] U.S. Cl. .................... 128/2 A; 128/325; 128/348
[58] Field of Search .............. 128/2 A, 2 M, 2.05 R, 128/348–351, 325, 344, 276, 214 R, 214.4; 138/93; 137/861, 863, 872, 874

[56] References Cited

U.S. PATENT DOCUMENTS

| | | | |
|---|---|---|---|
| 3,071,137 | 1/1963 | Niebel et al. | 128/276 |
| 3,392,722 | 7/1968 | Jorgensen | 128/350 R X |
| 3,417,744 | 12/1968 | Miskin et al. | 128/2 A |
| 3,834,394 | 9/1974 | Hunter et al. | 128/348 X |

FOREIGN PATENT DOCUMENTS

| | | | |
|---|---|---|---|
| 72860 | 5/1970 | German Democratic Rep. | 128/348 |
| 368151 | 6/1974 | Sweden | 128/2 A |

*Primary Examiner*—Dalton L. Truluck
*Attorney, Agent, or Firm*—McDougall, Hersh & Scott

[57] ABSTRACT

A catheter apparatus with occlusion and flow diverting valve means for controlling the flow of fluid into a tube including a conduit to lead fluid into cylindrical tube, a bag-like member made of resilient material and arranged to close an opening of the top of the conduit, a valve means provided on the conduit and a connecting means to connect the bag-like member and the valve means. Settling this apparatus in the cylindrical tube, when fluid is forced to flow into the bag-like member through the conduit, the bag-like member expands, whereby the cylindrical tube is closed and the valve means is opened to flow fluid out of the conduit.

8 Claims, 8 Drawing Figures

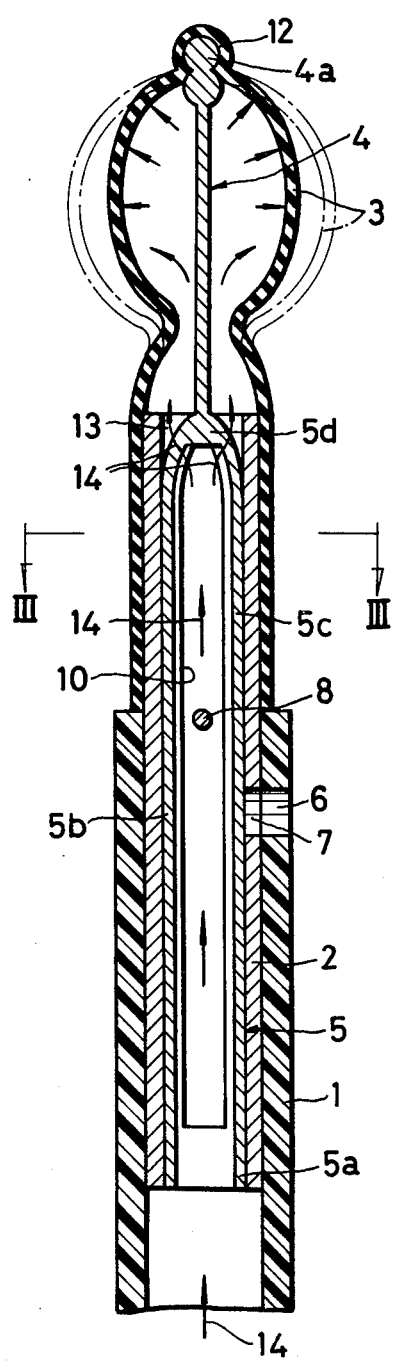
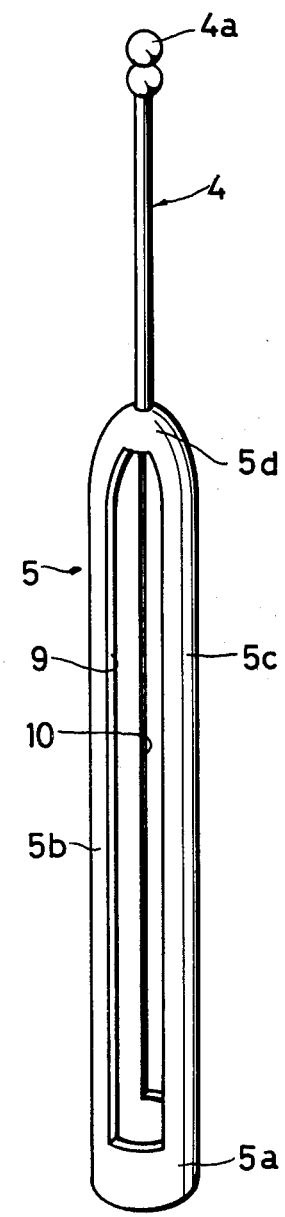
FIG. 1
FIG. 2

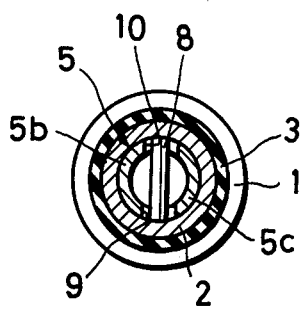
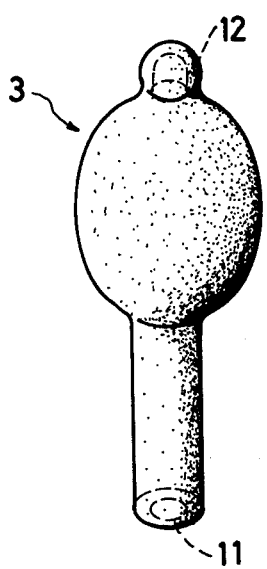
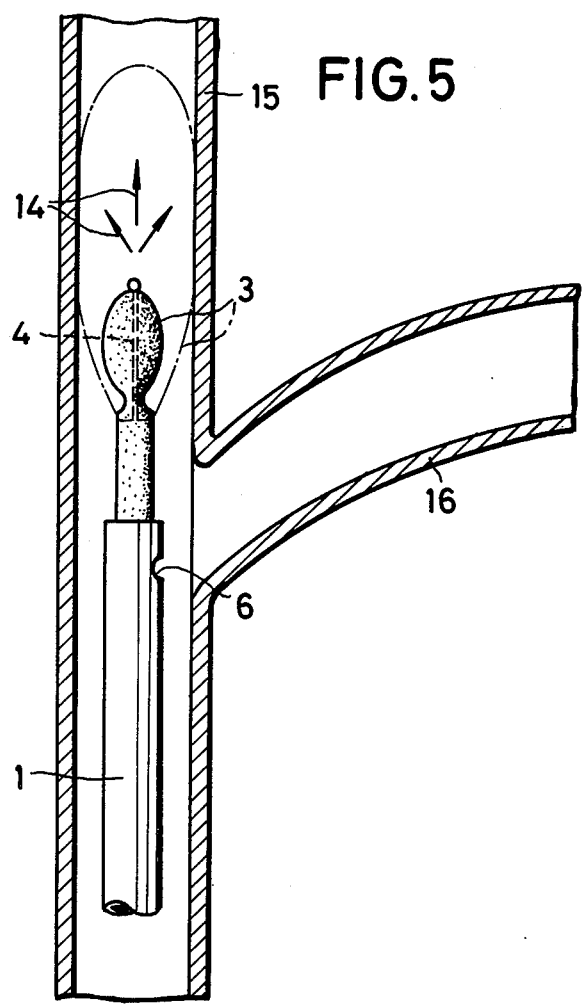

4,137,906

CATHETER APPARATUS WITH OCCLUSION AND FLOW DIVERTING MEANS

BACKGROUND OF THE INVENTION

1. Field of the Invention

This invention relates to an apparatus for fluid to flow into cylindrical tube, and specially, is suitable for X-ray contrast medium to flow into a blood vessel.

2. Description of the Prior Art

When the X-ray contrast medium is put into an artery for an internal organ, absorbing rate of X-ray of the internal organ varies from that of other internal organs. Therefore for example, shape or details of a liver can be observed by X-ray. But, as the liver is connected with a heart by an artery, the contrast medium flows not only into the liver but also into the heart. The contrast medium must selectively be flowed into the liver only. But up to this time, no apparatus have been offered to flow X-ray contrast medium selectively to the liver.

SUMMARY OF THE INVENTION

An object of this invention is to provide a novel apparatus for fluid to flow selectively into a cylindrical tube.

Another object of this invention is to provide a novel apparatus specially for X-ray contrast medium to flow selectively to a predetermined internal organ.

A further object of this invention is to provide a novel apparatus for fluid to flow selectively into a cylindrical tube, in which the selection of the flow of the fluid is controlled automatically.

A still further object of this invention is to provide a novel apparatus for fluid to flow selectively into a cylindrical tube which can be easily treated.

The invention more specifically comprises a catheter apparatus including an occlusion and flow diverting valve means for controlling the flow of fluid within an artery or other tube-like member. The apparatus is located, for example, in a cylindrical tube, and a conduit is provided to lead fluid into the cylindrical tube, a bag-like member made of resilient material is arranged to close an opening of the top of the conduit, and a valve means is provided on the conduit and a connecting means to connect the bag-like member and the valve means. Settling this apparatus in the cylindrical tube, when fluid is forced to flow into the bag-like member through the conduit, the bag-like member expands, whereby the cylindrical tube is closed and the valve means is opened to flow fluid out of the conduit.

The above and other objects, features and advantages of this invention will become apparent from the following detailed description of illustrative embodiments shown in the accompanying drawings.

BRIEF DESCRIPTION OF THE DRAWINGS

FIG. 1 to FIG. 6 show an apparatus according to one embodiment of this invention, and in this embodiment, the invention is applied to an apparatus for X-ray contrast medium to flow into a blood vessel.

FIG. 1 is a vertical longitudinal sectional view of the apparatus for X-ray contrast medium to flow into a blood vessel;

FIG. 2 is a perspective view of a valve means of the apparatus;

FIG. 3 is a cross sectional view of the apparatus, taken along the line III — III of FIG. 1;

FIG. 4 is a perspective view of a bag-like member of the apparatus;

FIG. 5 is a front view of the apparatus settled in an artery which is shown sectionally;

FIG. 6 is a vertical longitudinal sectional view of the apparatus which is settled in an artery and wherein the X-ray contrast medium is forced to flow into another artery;

FIG. 7 is a vertical longitudinal sectional view of the apparatus for X-ray contrast medium to flow into a blood vessel according to this modification;

FIG. 8 is a perspective view of a valve means of this modified apparatus.

DESCRIPTION OF THE PREFERRED EMBODIMENTS

Figure 6:
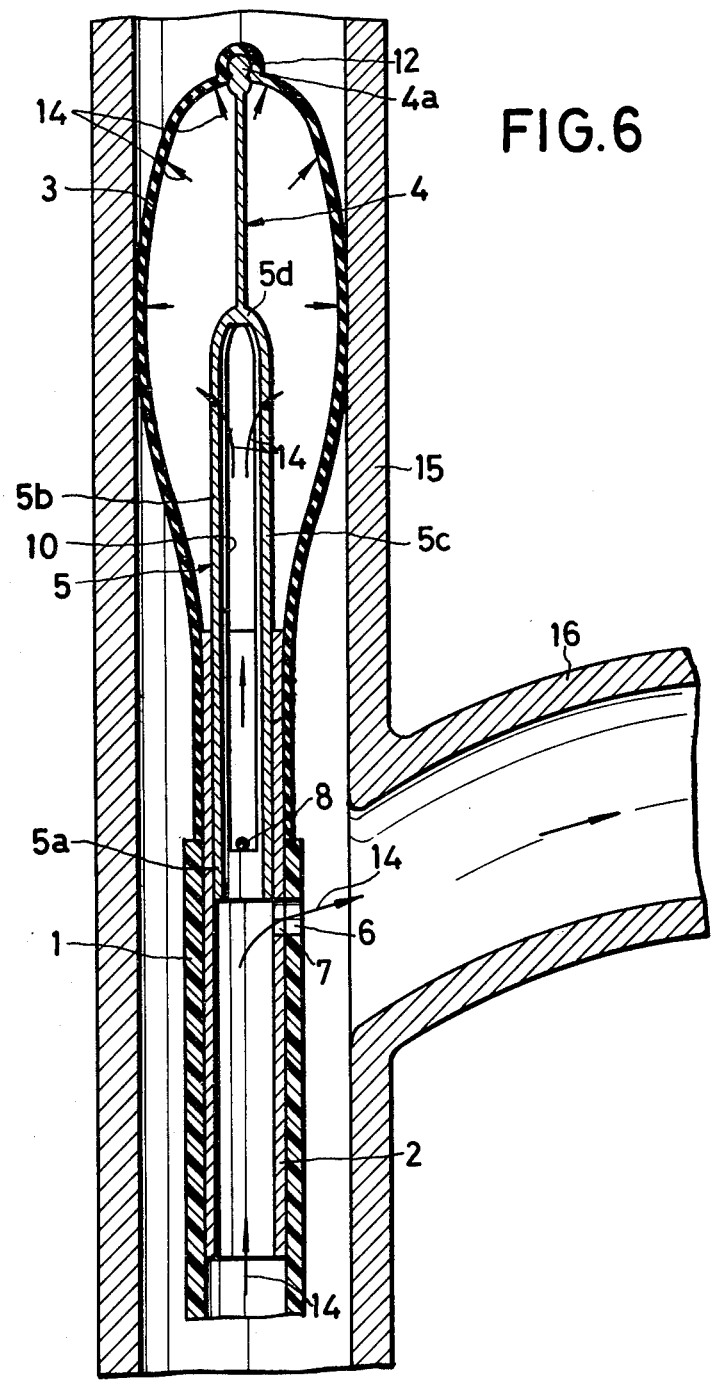

Referring to FIG. 1–FIG. 6, one embodiment of this invention will be described. In this embodiment, this invention is applied to an apparatus for X-ray contrast medium to flow into a blood vessel.

Firstly, the constitution of the apparatus according to this embodiment will be described in reference to FIG. 1–FIG. 3.

This apparatus comprises a conduit 1 made of polyethylene and connected to a supplying apparatus (not shown) of X-ray contrast medium, a pipe 2 made of stainless steel and fixed at the top of the conduit 1, a resilient bag-like member 3 made of semitransparent silicone resin fitted at the exposed part of the pipe 2, and a valve means 5 provided inside of the pipe 2 and connected with the bag-like member 3 by a bar 4 made of stainless steel.

A round opening 6 is formed at the top side of the cylindrical wall of the conduit 1, and on the cylindrical wall of the pipe 2, is defined a round opening 7 which is the same size as the opening 6 and aligned with the latter. At the inside of the pipe 2, a stopper pin 8 is fixed a little apart from the opening 7 to regulate the movement of the valve means 5. The valve means is formed cylindrically, as apparently shown in FIG. 2, and this cylindrical valve means has a pair of longitudinal slits 9 and 10, whereby a pair of arc shaped walls 5b and 5c is formed. The stopper pin 8 passes through the slits 9, and 10. At the bottom end 5a of the valve means 5, the longitudinal slits 9 and 10 terminate. The valve means is tapered and substantially conical at the top 5d of the cylinder 5. The bar 4 is fixed at the conical top 5d of the cylinder 5.

The bag-like member 3 is spindle-shaped, as shown in FIG. 4, before it is fitted to the pipe 2. The bar 4 is inserted from a bottom opening 11 of the member 3 to fit a spherical portion 4a formed integrally with the top of the bar 4 into a spherical hollow 12 defined at the top of the bag 3. And the bottom portion of the bag 3 is drawn out downwardly to make the bottom cylindrical portion of the bag 3 adhere closely on the outer cylindrical surface of the pipe 2. If a thread is wound on the surface of the pipe 2 before the bag-like member 3 is attached, the bag-like member 3 is surely held by the frictional force of the thread and by the contracting force of silicone resin. Other methods also may be adopted for fixing the bag 3 on the pipe 2.

The cylindrical valve means 5 is slidably supported longitudinally by the inner surface of the pipe 2, and the arc shaped wall 5c closes the opening 7 of the pipe 2 and the opening 6 of the conduit 1. Accordingly, a valve mechanism is constituted by the cylinder 5 and the pipe 2. On the other hand, top 5d of the cylindrical valve 5 is conical, and outer surface of the valve 5 is separated from the inner surface of the pipe 2 to form a gap 13. Therefore, if X-ray contrast medium 14 is supplied through the conduit 1, the medium flows into the bag 3 through the cylinder 5, slits 9 and 10 and the gap 13.

Next, the operation of this apparatus will be described.

Firstly as shown in FIG. 5, the above mentioned apparatus is inserted into the branching point of the artery through the cut-out end (not shown) of the artery, where the artery branches into two arteries one 15 of which is connected to the heart and the other 16 to the liver. On this inserting operation of the apparatus, the position of the apparatus is observed by X-ray so that the apparatus locates at the branching point of the artery and the opening 6 faces with the artery 16.

Next, the X-ray contrast medium is forced to flow into the apparatus through the conduit 1, and then the medium 14 flows into the bag-like member 3 as shown in FIG. 1. Therefore, the bag-like member 3 is filled with the medium, and the medium 14 presses the wall of the bag 3 outwardly. As the bag-like member 3 is made of resilient material, the member 3 expands as shown by the dot-dash line on FIG. 1. At the first stage of the expansion of the bag 3, the bag 3 contacts with the inner wall of the artery 15, whereby the artery 15 is closed perfectly by the bag 3. In this stage, the bag 3 expands substantially in the lateral direction and not in the longitudinal direction, and the cylinder valve 5 keeps the position shown in FIG. 1. Accordingly, the X-ray contrast medium 14 does not flow out of the apparatus through the openning 6 of the conduit 1.

Further, the X-ray contrast medium 14 is forced to flow into the apparatus, the bag 3 expands longitudinally because the bag 3 is restrained from expanding laterally by the wall of the artery 15. That is, at the second stage of the expansion of the bag 3 the bag 3 streches toward the heart. As the bag 3 and the cylinder valve 5 are connected to each other by the bar 4, the cylinder valve 5 is forced to go upwards, in accordance with the expansion of the bag 3 in this stage. And then the bottom ends of the longitudinal slits 9 and 10 engage with the stopper pin 8 mounted inside the pipe 2, to prevent further movement of the cylinder valve 5 as shown in FIG. 6. In this situation, the bottom end of the cylinder valve 5 is located substantially at the top of the conduit 1, to open the openings 6 and 7. These movements happen almost instantaneously. As the valve means 5 opens the openings 6 and 7, the X-ray contrast medium flows out of the apparatus into the blood vessel 16. In this stage, as the contrast medium 14 is continuously forced to flow into this apparatus to keep the bag 3 in the expanded state, the artery 15 to the heart is closed, and the contrast medium can not flow towards the heart. Consequently, the X-ray contrast medium can be selectively led to the liver through the artery 16.

After the predetermined quantity of X-ray contrast medium is poured, the supplying of the medium is ceased. Then the bag 3 is deflated. And when the bag 3 is deflated in the longitudinal direction of the blood vessel 15, the valve means 5 slides downwards to close the opening 7 of the pipe 2 and the opening 6 of the conduit 1. Therefore, the medium ceases to flow out of the apparatus. And in this instance, as the medium poured into the artery 16 has been already led to the liver with the blood, the medium may not flow to the heart, even though the artery 15 is opened by the contraction of the bag 3.

As mentioned above, according to this embodiment, the resilient bag 3 connected with the valve means 5 expands to close the artery 15 and to open the valve, and thereby the X-ray contrast medium is led selectively to the liver. Further, this operation can be attained automatically by forcing the medium to flow.

Next, a modification of this embodiment will be described in reference to FIG. 7 and FIG. 8.

In this modification, the structure of the valve-means 5 is modified.

As illustrated, the valve 5 comprises solid walls with transverse member 18 extending across the open top of the cylinder. The member 18 supports a button 17, and legs 4 extend from the button for connection of the spherical member 4a.

Figure 7:
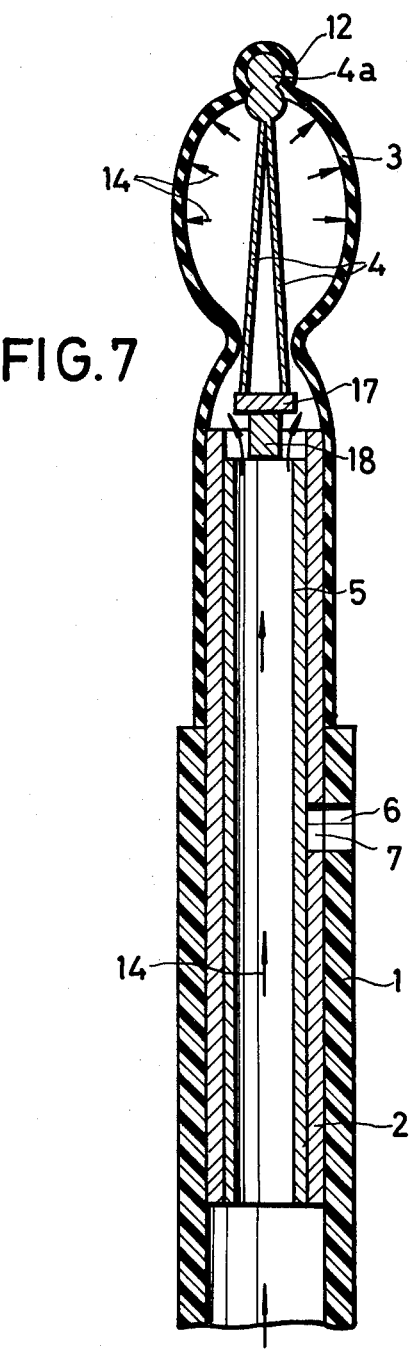
FIG. 7 and FIG. 8 show a modification of this apparatus according to the embodiment of this invention.
Figure 8:
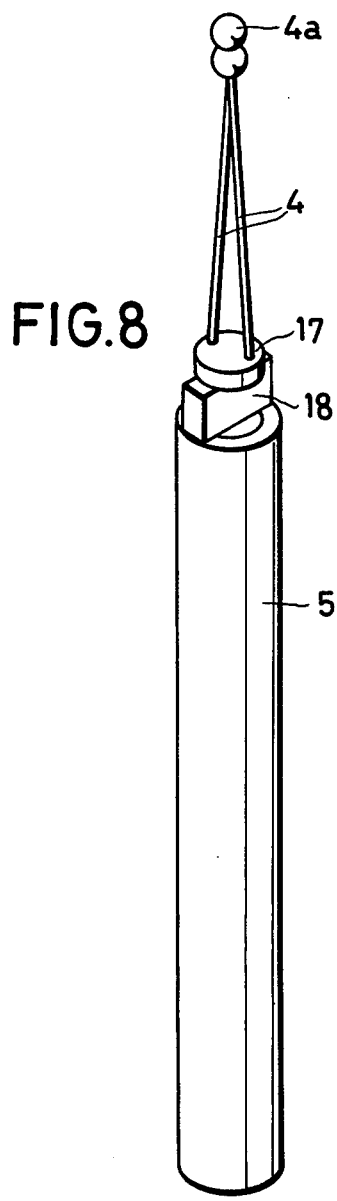

The structure of FIGS. 7 and 8 functions in substantially the same manner as the first embodiment described. The only difference is that the fluid exits through the open top of the cylinder 5 into the bag-like member 3 for achieving expansion and occlusion. Furthermore, the fluid drives the cylinder 5 upwardly as the bag 3 expands further whereby the fluid will eventually be caused to flow through openings 6, 7.

One contemplated modification of the invention involves the elimination of pipe 2. In that case, of course, the cylindrical structure 5 will slide in engagement with conduit 1. Furthermore, the structure is not limited to use in conjunction with the particular fluid referred to above.

While there have been described preferred embodiments of the invention, obviously modifications and variations are possible in light of above teachings. It is therefore to be understood that within the scope of appended claims, the invention may be practiced otherwise than as specifically described.

What is claimed is:

1. A catheter apparatus with occlusion and flow diverting valve means for selectively directing fluid within a tube, said construction comprising a conduit for said fluid, an opening defined by a wall of the conduit, a resilient bag-like member at one end of said conduit whereby said fluid is adapted to be delivered into the bag-like member, valve means supported in said conduit, connecting means connecting said bag-like member to said valve means, said valve means being slideable longitudinally of said conduit for movement between a position closing said opening and a position opening said opening, said fluid being delivered into said bag-like member when said opening is closed and said bag-like member being thereby expandable by the pressure of said fluid for engagement of the outer surfaces of the bag-like member with the inner walls of said tube to thereby prevent passage of fluid around and beyond the bag-like member, the movement of said bag-like member and associated connecting means simultaneously sliding said valve means to said position opening said opening whereby said fluid is directed through said opening.

2. An apparatus according to claim 1 wherein said tube defines a branch tube, said apparatus being located whereby fluid directed through said opening flows into said branch tube.

3. An apparatus according to claim 1 wherein said valve means comprises a cylindrical member slideable longitudinally in said conduit.

4. An apparatus according to claim 3 further comprising cooperating stop means supported by said conduit and by said cylindrical member to limit the sliding movement of said cylindrical member to a point just sufficient to open said opening.

5. An apparatus according to claim 1 further comprising a pipe received within said conduit, said pipe extending outwardly of said conduit, and said bag-like member being connected to said pipe.

6. An apparatus according to claim 1 wherein a spherical hollow is formed at the top of said bag-like member, and a spherical ball formed at the end of said connecting means for receipt within said spherical hollow for thereby connecting said bag-like member to said valve means.

7. An apparatus according to claim 3 wherein the top of said cylindrical member is tapered to form a gap between the cylindrical member and the inner wall of said conduit, and openings formed in the sides of said cylindrical member communicating with said gap whereby said fluid flows from said conduit into said bag-like member by passing through the openings defined by the cylindrical member and through said gap.

8. An apparatus according to claim 3 including means supporting said connecting means at the top of said cylindrical member, said cylindrical member also defining an opening at its top for passage of fluid from the cylindrical member into the bag-like member.

* * * * *